(12) United States Patent
Dodds et al.

(10) Patent No.: US 7,544,377 B2
(45) Date of Patent: *Jun. 9, 2009

(54) CHEWABLE COMPOSITIONS WITH FAST RELEASE MAGNOLIA BARK EXTRACT

(75) Inventors: Michael W. J. Dodds, LaGrange Park, IL (US); James Roy Maxwell, Chicago, IL (US); Michael J. Greenberg, Northbrook, IL (US); Minmin Tian, Naperville, IL (US)

(73) Assignee: GIC Innovations Company, Chicago, IL (US)

( * ) Notice: Subject to any disclaimer, the term of this patent is extended or adjusted under 35 U.S.C. 154(b) by 30 days.

This patent is subject to a terminal disclaimer.

(21) Appl. No.: 11/602,123

(22) Filed: Nov. 17, 2006

(65) Prior Publication Data

US 2007/0134168 A1 Jun. 14, 2007

Related U.S. Application Data

(60) Provisional application No. 60/742,361, filed on Dec. 2, 2005.

(51) Int. Cl.
*A61K 36/00* (2006.01)

(52) U.S. Cl. .................. 424/775; 424/439; 424/441

(58) Field of Classification Search .............. None
See application file for complete search history.

(56) References Cited

U.S. PATENT DOCUMENTS

| | | | |
|---|---|---|---|
| 4,547,361 A | 10/1985 | Steltenkamp et al. | |
| 4,820,544 A | 4/1989 | Barcelon et al. | |
| 5,286,500 A | 2/1994 | Synosky et al. | |
| 5,939,050 A | 8/1999 | Lyer et al. | |
| 5,948,430 A | 9/1999 | Zerbe et al. | |
| 6,248,309 B1 | 6/2001 | Lyer et al. | |
| 6,280,751 B1 | 8/2001 | Fletcher et al. | |
| 6,284,264 B1 | 9/2001 | Zerbe et al. | |
| 6,495,512 B1 | 12/2002 | White et al. | |
| 6,500,409 B1 | 12/2002 | Scherl et al. | |
| 6,582,735 B2 | 6/2003 | Stogniew et al. | |
| 6,645,535 B2 | 11/2003 | Zyck et al. | |
| 6,703,000 B2 | 3/2004 | Ning et al. | |
| 6,719,962 B2 | 4/2004 | Day et al. | |
| 6,726,897 B2 | 4/2004 | Lawlor et al. | |
| 7,025,983 B2 | 4/2006 | Leung et al. | |
| 2002/0131990 A1 | 9/2002 | Barkalow | |
| 2005/0008690 A1 | 1/2005 | Miller | |
| 2006/0193909 A1* | 8/2006 | Stawski et al. | .............. 424/464 |

FOREIGN PATENT DOCUMENTS

| | | |
|---|---|---|
| CN | 1094895 A | 11/1994 |
| CN | 1096694 | 12/1994 |
| CN | 1096695 | 12/1994 |
| CN | 1096699 | 12/1994 |
| CN | 93111461.6 | 12/1994 |
| CN | 94110006.5 | 12/1994 |
| CN | 1115212 | 1/1996 |
| CN | 94116766.6 | 1/1996 |
| CN | 1141194 A | 1/1997 |
| CN | 1073410 C | 10/2001 |
| GB | 1311060 | 3/1973 |
| JP | 84-175422 | 10/1984 |
| JP | 2002-0003413 | 1/2002 |
| WO | WO 97/35599 | 10/1997 |
| WO | WO 99/51093 | 10/1999 |
| WO | WO 01/82922 A1 | 11/2001 |
| WO | WO 01/85116 A2 * | 11/2001 |
| WO | WO 02/072114 A2 | 9/2002 |
| WO | WO 02/091848 A1 | 11/2002 |
| WO | WO 2004/000235 | 12/2003 |

OTHER PUBLICATIONS

Sharma A. et al., 2005, *Oral Microbiology and Immunology* 20: 39-42.
Chang B. et al., 1998, *Planta Medica* 64: 367-369.
Schreiner H.C. et al., 2003, *PNAS* 100: 7295-7300.
Rickard A.H. et al., 2003, *Trends in Microbiology* 11: 94-100.

* cited by examiner

*Primary Examiner*—Christopher R. Tate
*Assistant Examiner*—Deborah A. Davis
(74) *Attorney, Agent, or Firm*—Brinks Hofer Gilson & Lione

(57) ABSTRACT

A chewable oral composition for oral cleansing, breath freshening, and antimicrobial benefits includes fast release Magnolia Bark Extract in combination with a surface active agent. The effectiveness of Magnolia Bark Extract in inhibiting biofilm formation in the oral cavity is increased by a synergistic combination of the rapidly released Magnolia Bark Extract with a surface active agent in a chewable oral cavity delivery agent, such as chewing gum, chewable candy, and a soft tablet. The fast release of the antimicrobial agents is effectuated by encapsulation or coating of the oral cavity delivery agent.

25 Claims, No Drawings

CHEWABLE COMPOSITIONS WITH FAST RELEASE MAGNOLIA BARK EXTRACT

RELATED U.S. APPLICATION

This application claims priority to U.S. provisional patent application Ser. No. 60/742,361, filed Dec. 2, 2005.

TECHNICAL FIELD

The present invention relates, in general, to confectionary compositions and, more particularly, to confectionary compositions containing Magnolia Bark Extract for oral care, and to methods of making and using the confectionary compositions.

BACKGROUND

There is considerable consumer demand for products that freshen breath and kill bacteria in the mouth. An oral product with breath freshening and bactericidal benefits is a convenient delivery for oral cleansing in the oral cavity and freshening breath. Bacteria in the oral cavity, particularly on the tongue, can generate volatile sulfur compounds, which are a major cause of bad breath. Of course, breath freshening is a very important part of everyday life.

In order to facilitate proper oral hygiene, oral cleansing and breath freshening practices should be conducted repeatedly throughout the day. However, oral cleansing and breath freshening may be difficult or inconvenient at times, depending on the nature of the breath freshening desired and the situation in which the breath freshening must occur. Brushing, flossing, cleaning one's tongue and gargling using a variety of devices and compositions are common oral care practices well-suited for the privacy of one's home. But, such devices and compositions are less convenient to use away from the home where bathroom facilities might be scarce, unavailable or unsanitary.

Dental plaque is a microbial deposit that forms on teeth within a short time of brushing. It has been described by researchers as a soft, concentrated mass consisting mainly of a large variety of bacteria together with a certain amount of cellular debris which develops within a short time of refraining from tooth brushing. Dental plaque is not removed by rinsing with water. More recently, dental plaque has been described as a diverse community of micro-organisms found on the tooth surface as a biofilm. The biofilm is embedded in an extracellular matrix of polymers that originate from both the tooth surface and the microbial organisms. It is generally recognized that a reduction in dental plaque promotes clean teeth, fresh breath, and healthy gums. The dental plaque biofilm, however, is very resistant to antimicrobial agents.

Antimicrobial agents that have been shown to have definite plaque-reducing abilities include chlorhexidine, cetylpyridinium chloride (CPC), Triclosan and Delmopinol. These are all medicinal and non-natural agents. Essential oils such as thymol, eucalyptol, methyl salicylate, and menthol along with other essential oils in an alcohol-based vehicle have also been found to reduce plaque. While thymol is most effective in reducing plaque, it has a disagreeable taste. Generally, these oils benefit from the presence of an alcohol to facilitate their solubility and penetration of the plaque biofilm. While suitable for oral treatments, such as mouthwashes, high concentrations of alcohols can leave a bitter aftertaste in oral compositions such as gums, edible films, confectioneries, and the like.

An active ingredient, or a combination of active ingredients, that can provide the benefits of either removing plaque, preventing or slowing down plaque formation, or that has an anti-inflammatory effect that would help maintain the healthy state of the gums, would promote health gums and fresh breath. It is known to incorporate active agents into chewing gums for the purpose of providing oral benefits including breath freshening and bactericidal properties. Such systems have the advantage of providing rapid, effect, and convenient delivery.

BRIEF SUMMARY

The present invention is directed towards a breath freshening composition which can be used in different comestible, confectionery products. One aspect of the present invention is directed towards the use of confectionary products for humans, such as chewing gums, chewable candies, and soft tablets, or confectionary products for animals, such as dog biscuits, wherein the confectionery products contain a breath freshening composition of the present invention.

In accordance with the present invention it has been unexpectedly discovered that Magnolia Bark Extract in combination with certain surface active agents is synergistically effective in inhibiting the growth of plaque-causing bacteria. The combination of Magnolia Bark Extract and selected surface active agents shows enhanced antiplaque growth activity in excess of either Magnolia Bark Extract or the surface active agent alone.

The present invention further relates to confectionary compositions containing fast release Magnolia Bark Extract in combination with a surface active agent intended for bactericidal and breath freshening properties. More specifically, the present invention relates to a fast release oral cavity delivery agent, such as a chewing gum, chewable candy, soft tablet, or other comestible product containing an effective amount of Magnolia Bark Extract in combination with a surface active agent, by which the inventive composition effectively inactivates or kills oral bacteria and freshens breath through the consumption of the chewable comestible product. The surface active agent is added to the chewable comestible product to synergistically increase the effectiveness of the Magnolia Bark extract.

In one aspect of the invention a confectionary composition for freshening the breath of consumers of the chewing gum includes a fast release oral cavity delivery agent and an effective amount of an antimicrobial agent comprising a synergistic ratio of Magnolia Bark Extract and surface active agent, wherein the synergistic ratio is at least about 1 part Magnolia Bark Extract to 1 part surface active agent.

Suitable surface active agents include salts of potassium, ammonium, or sodium. Sodium salts include anionic surfactants, such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

In another aspect of the invention, a process for preparing an oral care composition is provided. The process includes incorporation of an antimicrobial agent in the form of a synergistic ratio of Magnolia Bark Extract and surface active agent into a formulation in the amount of about 0.05% to about 10% by weight, based on the weight of the total formulation, admixing the ingredients until a uniform mixture is obtained and thereafter forming the mixture into suitable coating for an oral composition.

In yet another aspect of the invention, the process for preparing an oral care composition includes incorporation of an antimicrobial agent in the form of a synergistic ratio of Magnolia Bark Extract and surface active agent into a formulation in the amount of about 0.05% to about 10% by weight, based on the weight of the total formulation, and encapsulating the antimicrobial agent in an oral composition.

DETAILED DESCRIPTION

It is known to use chewable confections such as chewing gums as a vehicle for delivering components to the oral cavity that provide oral benefits such as breath freshening and bactericidal properties. Such systems have the advantage of providing a consumer with a convenient and inexpensive method for maintaining oral health and fresh breath throughout the course of the day.

The present invention is directed to chewable confectionary compositions that have antimicrobial properties, comprising fast release Magnolia Bark Extract and a surface active agent. The invention is further directed to a method of reducing or eliminating microorganisms present in the oral cavity, comprising masticating in the oral cavity a chewable confectionary product which comprises Magnolia Bark Extract and a surface active agent. Suitable confectionary products include chewing gums, chewy candies, soft tablets, and biscuits, which contain fast release Magnolia Bark Extract and a surface active agent according to the present invention.

The term "masticating" includes operations by which a comestible product is wholly or partially consumed while it is being held in the mouth, such as by chewing, sucking, or dissolving. Holding the product in the mouth for longer periods of time is expected to be associated with greater reduction of the microorganisms present in the oral cavity. Suitably effective periods of time for mastication range from 3-5 minutes, up to 20-30 minutes.

The phrase "fast release" as used in this specification and appended claims refers to the action of comestible ingredients that have a release rate faster than that of chewable comestibles, for example chewing gums treated by conventional coating processes. Typically, fast release action is created by ingredients that are released first from the comestible, for example the antimicrobial ingredient of this invention included in the chewing gum.

The present invention incorporates rapidly released Magnolia Bark Extract as the active component for oral bactericidal benefits. Magnolia Bark Extract is known to have bactericidal and antifungal properties. For example, magnolol and honokiol are two components in Magnolia Bark Extract with known antimicrobial activity.

The Magnolia Bark Extract used in the present invention may be obtained from O'Laughlin Industries, Co. LTD, Guang Zhou Masson Pharmaceutical Co., or Honsea Sunshine Bioscience and Technology Co. The Magnolia Bark Extract is obtained in the form of powder. The Magnolia Bark Extract is dissolved with the flavor and may be warmed to dissolve prior to making the oral product. Magnolia Bark Extract can be formulated using standard formulation techniques into a variety of oral care products.

While it is relatively easy to kill bacteria in solutions, the plaque biofilm is a complex environment that provides protection from environmental threat to bacteria, as well as synergies between bacterial species (Sharma A. et al., 2005, *Oral Microbiology and Immunology* 20: 39-42). Therefore, compared to a simple germ kill test, it is much harder to show actual efficacy against established plaque by an antimicrobial agent. Diffusion into the biofilm is limited, and bacteria within the bulk of the biofilm are protected from exposure to the agent by extracellular material, such as the glucan and dextran polysaccharides. It is, therefore, arguably easier to prevent formation of plaque than it is to remove an established plaque.

In accordance with the present invention, the antimicrobial effects of Magnolia Bark Extract are enhanced through the combination of Magnolia Bark Extract with a surface active agent. Although not intending that the invention be limited to any particular theory, it is believed that the combination of a surface active agent with an effective amount Magnolia Bark Extract can provide a chewable product that promotes the reduction of biofilms in dental plaques and in other areas of the oral cavity, such as the tongue. It is believed that the combination of Magnolia Bark Extract and a suitable surface active agent may prevent bacterial attachment to the acquired pellicle. Such a chewing gum can slow down or prevent plaque accumulation. Further, the chewable product of the invention can be effective in the removal of existing plaque in combination with enzymes, additional surface active agents, abrasives or combinations thereof.

A preferred surface active agent is one that increases the solubility of Magnolia Bark Extract and that can be used as a food additive. Suitable surface active agents include but are not limited to common surfactants, soaps, wetting agents, and emulsifiers. Some examples of surfactants include but are not limited to salts of potassium, ammonium, or sodium. Sodium salts include anionic surfactants, such as such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

The chewable product can also include additional breath freshening or oral health ingredients, which can be antimicrobial in nature. Further, the additional breath freshening or oral health ingredients can comprise food acceptable salts of zinc or copper, cooling agents, pyrophosphates or polyphosphates, and the like.

The invention also includes a treatment method for reducing the number or activity of bacteria in the oral cavity of a consumer. The method includes the steps of providing a chewable product that includes Magnolia Bark Extract in an amount sufficient to kill or deactivate oral bacteria in combination with a surface active agent and causing a person in need of the treatment to consume the chewing gum. The bacteria in the oral cavity of the person is reduced or inactivated by the treatment.

In one form, the chewable product is formulated with a fast release oral cavity delivery agent to deliver at least about 0.001% to about 2.0% concentration of Magnolia Bark Extract to the oral cavity. In another form, the chewable product is formulated with an oral cavity delivery agent to deliver at least about 0.01% concentration of Magnolia Bark Extract to the oral cavity. One or more surface active agents are added to the chewable product so as to enhance the effectiveness of the chewable product in the delivery of an effective amount to the oral cavity.

In accordance with one embodiment of the invention, one or more surface active agents are present in the chewable product in a concentration range of about 0.001% to about 2.0%. In the chewable product, Magnolia Bark Extract is combined with a surface active agent in a synergistic ratio that provides enhanced germ-kill effectiveness. The synergistic ratio ranges from about 1 part Magnolia Bark Extract to 1 part surface active agent up to about 4 parts Magnolia Bark Extract to 1 part surface active agent. One particularly effective surface active agent is sodium lauryl sulfate, and a particularly effective synergistic composition is about 2 parts Magnolia Bark Extract to 1 part sodium lauryl sulfate.

Given that Magnolia Bark Extract is a hydrophobic compound, there are several oral cavity delivery agents that may be used to enhance the release of the Magnolia Bark Extract from the chewable product. For example, in a chewing gum, the confectionary composition base is hydrophobic, which also inhibits the release of the Magnolia Bark Extract. In the various embodiments of the inventive confectionary composition, the Magnolia Bark Extract is combined with a surface active agent and may be encapsulated, spray dried, or formulated into a coating, or combinations thereof in order to facilitate and speed the release of the Magnolia Bark Extract into the oral cavity.

To evaluate the effectiveness of Magnolia Bark Extract, in vitro tests were conducted with three subgingival plaque bacteria associated with oral malodor. The Minimum-Inhibitory-Concentrations (MIC) study protocol is as follows. Chlorhexidine was used as a positive control and sterile water was used as a negative control. Menthol and Tween 80 was used as a solvent for Magnolia Bark Extract. Tween 80 is the common name for Polysorbate 80. Ninety-six-well microtiter plates were used for this study. Each well contained $5 \times 10^5$ colony forming units/ml of bacteria, serially diluted agents and bacterial growth medium. All bacterial cultures were incubated at 37° C. and stationary. Bacterial growth was estimated spectrophotometrically at 660 nm, after 48 hours. The MIC for each test bacteria was defined as the minimum concentration of test compound limiting turbidity to less than 0.05 absorbance measured at 660 nm.

The Minimum-Bactericidal-Concentrations (MBC) were determined using the 96-well microtiter plate serial dilutions as described above for MIC studies. Serial dilutions of cultures in wells showing no visible growth were performed and 10 microliters of culture were plated in triplicate on blood agar plates. Viable colonies were scored after incubation of the plates for 48 hours at 37° C. For each test bacterium, the number of colony forming units/ml (CFU/ml) was determined in the initial inoculum. The MBC was defined as the lowest concentration of a test compound that killed at least 99.9% of the cells present in the initial inoculum.

The results of the studies performed to obtain MIC and MBC of Magnolia Bark Extract (MBE) are as follows. Against *Streptococcus mutans* a Magnolia Bark Extract of 90% had an MIC of 15.62 µg/ml. For *Porphyromonas gingivalis*, the 90% Magnolia Bark Extract had an MIC of 3.91 µg/ml, and the 65% Magnolia Bark Extract had an MIC of 7.82 µg/ml. For *Fusobacterium nucleatum* the 90% Magnolia Bark Extract had an MIC of 3.91 µg/ml and an MBC of 7.82 µg/ml. Against the same organism, the 65% Magnolia Bark Extract had an MIC and MBC of 7.82 µg/ml. Chlorhexidine was the positive control and produced an MIC and MBC of 1.25 µg/ml for all three bacteria. The solvent consisting of water with 10% methanol and 3.8% Tween 80 had no noticeable growth inhibitory effects on any of the three bacteria in the study.

It is also known that Magnolia Bark Extract is effective against *Actinobacillus actinomyecetemcomitans*, *Prevotella intermedia*, *Micrococcus luteus*, *Bacillus subtilis*, *Veillonella disper*, *Capnocytophaga gingivalis*, and periodontic microorganisms (Chang B. et al., 1998, *Planta Medica* 64: 367-369). Many of these human pathogens are associated with periodontal diseases (Schreiner H. C. et al., 2003, *PNAS* 100: 7295-7300). It is also known that many of the above-mentioned bacterial species co-aggregate to create biofilm (Rickard A. H. et al., 2003, *Trends in Microbiology* 11: 94-100).

Further to the results described above, the effect of Magnolia Bark Extract on biofilm formation and removal was compared with different herbal and natural ingredients. Comparative testing was performed using green tea extract, Oolong tea extract, Licorice, and Magnolia Bark Extract. The comparative testing included determining the solubility in water, ethanol, water:ethanol mixtures and other solvents (for example, Tween in water), MIC for growth of *S. mutans*, MIC for formation of *S. mutans* biofilm in 96-well plates, and the effect on detachment of *S. mutans* biofilm.

The green tea was soluble in water; all other substances were found to be soluble in a 2:1 water:ethanol mixture. Magnolia Bark Extract was also soluble in 0.01 µl of 50% Tween 80 in water.

To evaluate the effect on *Streptococcus mutans* biofilm formation, 96-well microtiter plates were used. Each well contained *S. mutans* ($5 \times 10^6$ CFU/ml), and was serially diluted with test compounds and growth medium (brain heart infusion broth (BHI) with 0.5% sucrose). The controls included inoculated growth medium without test compounds. All plates were incubated at 37° C. under aerobic condition with growth estimated spectrophotometrically (660 nm) after 48 h using a microtiter plate reader. Then, the supernatant containing unattached cells was removed from each wells by aspiration, the attached biofilm mass was dissolved with 200 µl 1 N NaOH and the optical density was measured at 660 nm using the microtiter plate reader. Chlorhexidine (40 µg/ml) was used as a positive control.

To further evaluate the effect on *S. mutans* biofilm detachment, sterile 96-well microtiter plates were used where each well was inoculated with *S. mutans* ($5 \times 10^6$ CFU/ml), growth medium (BHI supplemented with 0.5% sucrose), and incubated at 37° C. under aerobic condition for biofilm formation. After 48 hours, the non-attached supernatant was aspirated and serially diluted. Test compounds were added to the preformed biofilm and incubated at 37° C. under aerobic condition. The controls included solvent without test compounds. After 30 min, the supernatant was aspirated from wells and the biofilm remaining after treatment was dissolved in 200 µl 1 N NaOH, and quantitated at 660 nm using the plate reader. A chlorhexidine positive control was used. If detachment of the biofilm by action of the test compounds occurred, the spectrophotometric absorbance or optical density (OD) should show a decrease compared to the non-treated control.

The results of the comparative testing are show below in Table 1. The test results are presented in units of µg/ml for each of the compounds. In Table 1, and in the following Tables, Magnolia Bark Extract is designated as "MBE" and the chlorhexidine positive control is designated as "CHX."

TABLE 1

Comparative Effect on MIC and Biofilm (μg/ml)

| Test | Green tea | Oolong tea | Licorice | MBE | CHX |
|---|---|---|---|---|---|
| MIC growth | 250 | 1000 | 250 | 7.8 | 2.5 |
| MIC biofilm formation | 250 | 250 | 250 | 7.8 | 2.5 |
| MIC biofilm detachment | >1000 | >1000 | >10000 | >1000 | >10 |

The data shown in Table 1 indicates that none of the compounds tested were more effective than chlorhexidine at removing the established biofilm. The green tea extract, licorice extract and Magnolia Bark Extract may inhibit *S. mutans* biofilm by inhibiting bacterial growth, since MICs are identical for both growth and biofilm formation. The Oolong tea did not inhibit planktonic growth, but was more effective at inhibiting the biofilm. Magnolia Bark Extract was most effective at inhibition of both growth and biofilm formation and well within an order of magnitude of the chlorhexidine positive control.

Although useful to show the comparative effect of Magnolia Bark Extract on biofilm formation and MIC growth, the foregoing test procedure may not effectively mimic the in vivo exposure of an oral care product to a developing plaque biofilm. In an in vivo situation, the active could be exposed to the plaque for a defined period of time at a set frequency (for example, for 5 minutes, three times a day). Therefore, a series of comparative experiments were conducted to mimic the in vivo use of potential active ingredients. To perform the tests the saliva compositions listed below in Tables 2 and 3 were prepared.

TABLE 2

Saliva buffer composition (filter sterilize after preparation)

| Compound | mg/L |
|---|---|
| Ammonium chloride | 233 |
| Calcium chloride, dihydrate | 210 |
| Magnesium chloride, hexahydrate | 43 |
| Potassium chloride | 1162 |
| $KH_2PO_4$ (monobasic potassium phosphate) | 354 |
| Potassium thiocyanate | 222 |
| Sodium citrate | 13 |
| Sodium bicarbonate | 535 |
| Dibasic sodium phosphate, $Na_2HPO_4$ | 375 |
| Urea | 173 |

TABLE 3

Supplemented Saliva Medium (filter sterilize after preparation)

| Ingredient | wt. % |
|---|---|
| Whole saliva | 25 |
| Saliva buffer | 45 |
| Modified eagle medium (MEM) | 20 |
| Trypticase soy broth | 10 |

A mixed culture system that utilizes the bacteria from freshly-collected simulated whole saliva was used. Saliva cell pellets were used to inoculate saliva-coated hydroxyapatite (S-HA) discs. The discs were placed in 24-well cell culture plates and incubated for up to 3 days. Biofilms were exposed to actives on days 2 and 3 (starting at 18 hours), and quantified on day 4. The number of bacteria was determined by spectrophotometric absorbance or optical density (OD) at 600 nm. The five phases of the experiment were: pellicle formation; bacterial attachment; biofilm growth; exposure to actives; and bacterial enumeration.

To form the pellicles, HA Discs were ultrasonically washed in deionized water and air-dried, then autoclaved. The discs were placed in a 24-well plate with 1 ml 50% sterile saliva (1 part sterile whole saliva: 1 part saliva buffer, filter sterilize after preparation) for 2 hours on slow agitation at room temperature. The saliva was suctioned and then the discs were transferred to fresh wells for bacterial attachment.

To form the biofilms, the bacterial suspension was removed, and the discs were transferred to fresh wells. One ml of supplemented saliva medium was added and the plate was placed in the incubator for overnight incubation and for the duration of the experiment (up to 72 hours).

A stock solution of 1% Magnolia Bark Extract in 60% ethanol was prepared. Magnolia Bark Extract samples were prepared having a concentration range of 125, 250, 500, and 1000 μg/ml (ppm) in a Phosphate-Buffered-Saline (PBS) solution, where the negative control was PBS and the positive control was CHX having a concentration of 0.12%. The PBS control solution had a composition as shown below in Table 4.

TABLE 4

Phosphate Buffered Saline Composition

| Ingredient | g/L |
|---|---|
| NaCl | 8.0 |
| KCl | 0.2 |
| $Na_2PO_4$ | 1.44 |
| $KH_2PO_4$ | 0.24 |

One-ml quantities of active ingredients and controls were placed into fresh wells, and the discs were transferred to these wells for 5 minutes. The chlorhexidine control exposure was one minute, two times a day to mimic the standard mouthrinse procedure. The exposure to active ingredient was carried out at 8:00 AM, 12:00 and 4:00 PM. After the timed exposure, the solution was removed and the discs washed twice with PBS and then transferred to fresh medium. For some experiments, the medium used during the day was TSB (Tryptic Soy Broth) with a 50 μl 40% sterile sucrose solution added to each well (to give a 2% sucrose solution). The medium was not replaced after the mid-day exposure.

After overnight incubation (day 2), discs were exposed to controls and actives. On day 3 the biofilms were again exposed to tests and controls. On day 4 the discs were removed from the medium, the medium pH was measured to obtain an indication of metabolic activity, and the discs were placed into tubes with 2.5 ml PBS, vortexed for 20 sec, and then placed into the ultrasonic bath for another 20 sec. The suspension was transferred into cuvettes and the bacterial cell density determined by OD measurements at 600 nm.

The results of the pH measurements are shown below in Table 5 and the percentage reductions in OD compared to PBS control are shown below in Table 6.

TABLE 5 pH Measurements

| Test Sample | pH |
| --- | --- |
| PBS Control | 5.4 |
| CHX Control | 8.8 |
| MBE 125 | 5.2 |
| MBE 250 | 6.0 |
| MBE 500 | 7.1 |
| MBE 1000 | 7.6 |

TABLE 6

Percentage Reductions in Optical Density at 600 nm

| Test Sample | % OD reduction |
| --- | --- |
| PBS Control | 0 |
| CHX Control | 84 |
| MBE 125 ppm | −2 |
| MBE 250 ppm | 21 |
| MBE 500 ppm | 53 |
| MBE 1000 ppm | 59 |

The results shown above in Tables 5 and 6 illustrate a clear effect and dose-response of Magnolia Bark Extract on inhibition of biofilm metabolic activity (as determined by pH of the medium) and biofilm formation (OD). Chlorhexidine had a strong inhibitory effect on plaque metabolism and cell number. Magnolia Bark Extract was less effective than chlorhexidine, but the chlorhexidine concentration was slightly higher than the Magnolia Bark Extract.

To evaluate the effect of Magnolia Bark Extract in combination with the surface active agent, sodium lauryl sulfate, five active ingredient solutions were prepared using the procedures described above. The chlorhexidine control solution was prepared having a slightly reduced concentration of 0.1% (1000 ppm). Also, the MBE solutions were prepared to have a concentration of 500 ppm. Sodium lauryl sulfate was added to two of the Magnolia Bark Extract solutions to obtain SLS concentrations of 0.05% and 0.1% in the Magnolia Bark Extract solutions. The testing with Magnolia Bark Extract described above was repeated with the five solutions.

The pH test results are shown below in Table 7, where sodium lauryl sulfate is designated as "SLS."

TABLE 7 pH Measurements

| Test Sample | pH |
| --- | --- |
| PBS Control | 4.9 |
| CHX Control | 8.8 |
| SLS 1000 ppm | 5.7 |
| MBE 500 ppm | 7.1 |
| MBE 500 ppm/SLS 500 ppm | 5.9 |
| MBE 500 ppm/SLS 1000 ppm | 6.2 |

The percentage reductions in optical density (OD) test results are shown below in Table 8. Note that the data in the last row of this table were taken from a different experiment.

TABLE 8

Percentage Reduction in Optical Density at 600 nm

| Test Sample | % OD reduction |
| --- | --- |
| PBS Control | 0 |
| CHX Control | 94 |
| SLS 1000 ppm | 61 |
| MBE 500 ppm | 65 |
| MBE 500 ppm/SLS 500 ppm | 79 |
| MBE 500 ppm/SLS 1000 ppm | 70 |
| MBE 1000 ppm/SLS 500 ppm | 88 |

The results listed above in Tables 7 and 8 show that the chlorhexidine control had the highest-pH and this control also had the lowest OD. Based on pH data (an indication of metabolic activity), 500 ppm Magnolia Bark Extract alone was more inhibitory than the sodium lauryl sulfate or the Magnolia Bark Extract/sodium lauryl sulfate mixtures. The OD absorbance data (bacterial number), however, indicates a synergistic effect at reducing the biofilm in test solutions combining Magnolia Bark Extract and sodium lauryl sulfate. In particular, the results show that the 1000 ppm sodium lauryl sulfate and 500 ppm Magnolia Bark Extract had similar effects in terms of plaque quantity, although Magnolia Bark Extract inhibited plaque metabolic activity to a greater extent. The Magnolia Bark Extract with sodium lauryl sulfate at 500 ppm reduced plaque growth compared to 500 ppm Magnolia Bark Extract alone. Further, the sodium lauryl sulfate at 1000 ppm was less effective than at 500 ppm in combination with 500 ppm Magnolia Bark Extract. The most effective combination was 1000 ppm of Magnolia Bark Extract in combination with 500 ppm of sodium lauryl sulfate.

Although not wishing to be bound by any particular theory regarding the active mechanism of the invention, it is possible that the reason for the paradoxical effect of decreased cell mass with increased metabolic activity of the Magnolia Bark Extract/sodium lauryl sulfate mixtures relates to the action of the sodium lauryl sulfate in allowing more rapid penetration of the Magnolia Bark Extract into the biofilm, where it has an immediate germ kill and/or growth-inhibitory effect, but the Magnolia Bark Extract is also rinsed away more easily, so the substantivity and prolonged metabolic effect is minimized.

To evaluate the germ-kill efficacy and synergist effect when two or more germ-kill actives are combined, testing was performed to determine the ratio of MBE to surface active agent. The germ-kill active and/or surface active agent were dissolved in ethanol or sterile water to give an initial concentration 0.1% to 1%. The solution was diluted with a nutrient broth to give an initial concentration of 0.05% to 0.5%, which was then serially diluted two-fold so that each subsequent dilution contained 50% of the compound concentration of the previous dilution while maintaining a constant level of nutrients for each dilution. These dilutions were inoculated with representative oral microorganisms, or incubated saliva, and incubated for 24 hours at 37° C. For each surface active agent, the lowest dilution that was not turbid was registered as the MIC. The MBC was determined by transferring 10 microliter of liquid from non-turbid tubes to fresh growth media and incubated for 48 hours. For each surface active agent, the lowest dilution that did not demonstrate growth was considered the MBC.

Table 9 below shows the MIC of various surface active agents and emulsifiers on incubated saliva.

TABLE 9

Minimum-Inhibitory-Concentration of Selected Surface Active Agents

| Sample | MIC (ppm) |
|---|---|
| Sodium Lauryl Sulfate | 50 |
| Betaine BF-20 | >1000 |
| Tego Betain CKD | 25 |
| Tego Betain ZF | 25 |
| Sodium Brasslate | 500 |
| Sodium Lauroyl Sarcosinate | 100 |
| Sodium Stearoyl Lactylate | >3000 |
| Tween 20 | >1000 |
| Sucrose Stearate | >500 |
| Sucrose Distearate | >500 |
| Chlorhexidine gluconate* | 2 |

*used as a positive control

The results show that sodium lauryl sulfate and Cocamidopropyl Betaine are good germ-kill surface active agents, while sodium brasslate shows a moderate germ-kill efficacy. Sodium stearoyl lactylate, Polysorbate 20 (commonly known as Tween 20), Sucrose stearate, and Sucrose distearate are weak or non germ-kill actives.

To evaluate the synergistic effect of an active ingredient in combination with a surface active agent, the fractional inhibitory index (FIC) was computed according to equation (1) below:

$$FIC = [MIC_{A\text{-combined with }B}/MIC_{A\text{ alone}} + MIC_{B\text{-combined with }A}/MIC_{B\text{-alone}}] \quad (1)$$

where an FIC value of less than 1.0 is synergistic, an FIC between 1.0 and 2.0 is additive, and an FIC greater than 2.0 is antagonistic.

Table 10 below shows the MIC values for combinations of Magnolia Bark Extract/sodium lauryl sulfate and Magnolia Bark Extract/Tween-20 on *S. mutans*:

TABLE 10

Minimum-Inhibitory-Concentration of Selected Surface Active Agents

| Sample | MIC/ppm | FIC |
|---|---|---|
| Sodium Lauryl Sulfate | 100 | — |
| Magnolia Bark Extract | 25 | — |
| MBE/SLS 1/4 | 50 | 1 |
| MBE/SLS 3/2 | 25 | 0.70 |
| MBE/SLS 4/1 | 25 | 0.85 |
| MBE/Tween 20 100/100 | 25 | 1 |
| MBE/Tween 20 100/250 | >100 | >2 |
| MBE/Tween 20 100/500 | >100 | >2 |
| Chlorhexidine gluconate* | 2 | — — |

The results indicate that Magnolia Bark Extract and sodium lauryl sulfate show synergistic effect (FIC<1) when combined in a ratio (MBE/SLS) between about 1/4 to about 4/1. However, Magnolia Bark Extract and Tween-20 show antagonist effect (FIC>2) when combined.

In particular, the results show that certain ratios of Magnolia Bark Extract to sodium lauryl sulfate show synergistic effects. Accordingly, the present invention contemplates chewable products such as chewing gums that contain a synergistic ratio of Magnolia Bark Extract to a surface active agent. From the foregoing experimental results, Magnolia Bark Extract in combination with a surface active agent will produce a synergistic antimicrobial effect in a chewing gum. Chewing gums having a surface active agent in a concentration range of about 25 ppm to about 500 ppm in combination with Magnolia Bark Extract show synergistic properties for inhibiting the biofilm formation that leads to dental plaque. Further, chewing gums having a weight ratio of at least about one part Magnolia Bark Extract to one part surface active agent will produce a synergistic antimicrobial effect in a chewing gum. Further, the synergistic ratio of Magnolia Bark Extract to surface active agent can range from about 1 part Magnolia Bark Extract to 1 part surface active agent up to about 4 parts Magnolia Bark Extract to 1 part surface active agent. Accordingly, the present invention contemplates a wide range of chewing gums containing a synergistic combination of Magnolia Bark Extract and a surface active agent.

EXAMPLES

The examples listed below are not intended to exclude other variations in formulations and the present invention is not limited to these formulations.

Chewing Gum Formulations

In an embodiment of the present invention, an effective amount for antimicrobial benefit of fast release Magnolia Bark Extract in combination with a surface active agent, such as described above, is present in a chewing gum formulation. In one aspect of the present invention, the amount of Magnolia Bark Extract is present in an amount up to about 5% by weight of the chewing gum product. In another aspect of the present invention, the amount of Magnolia Bark Extract is about 1% of the weight of the chewing gum product. In yet another aspect, the Magnolia Bark Extract is present in the amount of 0.01% by weight of the chewing gum product. Considering the potency of Magnolia Bark Extract as described in the in vitro studies above, levels as low as about 0.005% by weight of the chewing gum product should be effective in bactericidal properties. The absolute amount of sodium lauryl sulfate in the chewing gum formulation can range from about 4 mg to about 10 mg.

In general, a chewing gum composition typically comprises a water-soluble bulk portion, a water-insoluble chewable gum base portion and typically water-soluble flavoring agents. The water-soluble bulk portion dissipates with a portion of the flavoring agent over a period of time during chewing. The gum base portion is retained in the mouth throughout the chew. For the formulation of this invention, beside the active substance, suitable compounds are used to increase the disintegration of the water soluble compounds facilitating in this way the dissolution (fast release) of the vehiculated active substance comprising MBE and food grade detergent.

The insoluble gum base generally comprises elastomers, resins, fats and oils, softeners and inorganic fillers. The gum base may or may not include wax. The insoluble gum base can constitute approximately about 5% to about 95% by weight of the chewing gum, more commonly the gum base comprises about 10% to about 50% of the gum, and in some preferred embodiments approximately about 25% to about 35% by weight, of the chewing gum.

In a preferred embodiment, the chewing gum base of the present invention contains about 20% to about 60% by weight synthetic elastomer, up to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with average molecular weight of about 10,000 to about 95,000, isobutylene-isoprene copolymer (butyl elastomer), styrenecopolymers having styrene-butadiene ratios of about 1:3 to about 3:1, polyvinyl acetate having average molecular weight of about 2,000 to about 90,000, polyisoprene, polyethylene, vinyl acetate vinyl laurate copolymer having vinyl laurate content of about 5% to about 50% by weight of the copolymer, and combinations thereof.

Preferred ranges for polyisobutylene are 50,000 to 80,000 average molecular weight; for styrene are 1:1 to 1:3 bound styrene; for polyvinyl acetate are 10,000 to 65,000 average molecular weight, with the higher molecular weight polyvinyl acetates typically used in bubble gum base; and for vinyl acetate laurate, a vinyl laurate content of 10%.

Natural elastomers may include natural rubber, such as smoked or liquid latex and guayule, as well as natural gums, such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva, and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha, beta, and/or any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono and triglycerides, acetylated monoglycerides, fatty acids (for example stearic, palmitic, oleic and linoleic acids), and combinations thereof.

Colorants and whiteners may include FD&C dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. Softeners, also known in the art as plasticizers or plasticizing agents, generally constitute between approximately 0.5% to about 15% by weight of the chewing gum. These include glycerin, propylene glycol, and aqueous sweetener solutions such as those containing sorbitol. Hydrogenated starch hydrolysate and corn or other starch hydrolysate syrups (sometimes called glucose syrups) and combinations thereof are particularly preferred as they also function as binders to improve the flexibility and other physical properties of the gum.

Bulk sweeteners, or bulking agents, include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide components commonly known in the chewing gum art, including but not limited to, sucrose, dextrose, maltose, dextrin, dried invert sugar, fructose, levulose, galactose, corn syrup solids, and the like, alone or in combination. Sugarless sweeteners include, but are not limited to, sugar alcohols such as sorbitol, mannitol, xylitol, hydrogenated starch hydrolysates, maltitol, erythritol, trehalose, tagatose, and the like, alone or in combination.

High intensity artificial sweeteners can also be used, alone or in combination, with the above. Preferred sweeteners include, but are not limited to, sucralose, aspartame, NAPM derivatives such as neotame, salts of acesulfame, altitame, saccharin and its salts, cyclamic acid and its salts, glycyrrhizinate, stevia, perillartine, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in a chewing gum. The softener may also provide additional sweetness such as with aqueous sugar or alditol solutions.

If a low calorie gum is desired, a low caloric bulking agent can be used. Examples of low caloric bulking agents include: polydextrose; raftilose, raftilin; fructooligosaccharides (NutraFlora); Palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise, and the like. Artificial flavoring agents and components may also be used. Natural and artificial flavoring agents may be combined in any sensorially acceptable fashion. Flavoring may include a cooling agent to enhance the flavor and perceived breath freshening of the product. Cooling agents include menthol, ethyl p-menthane carboxamide, N,2,3-trimethyl-2-isopryl-butanamide, menthyl glutarate (Flavor Extract Manufacturing Association (FEMA 4006)), menthyl succinate, menthol PG carbonate, menthol EG carbonate, menthyl lactate, menthone glyceryl ketal, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and combinations thereof.

In addition to the Magnolia Bark Extract and surface active agents of the present invention, active ingredients or medicaments may be added for various purposes. If the medicament or active is water soluble in the chewing gum, it preferably will include a base/emulsifier system which leads to the desired concentration of the medicament in the saliva (more hydrophilic balance). If the medicament or active is water insoluble, the chewing gum preferably includes a base/emulsifier system which leads to the desired concentration of the medicament in the saliva (more lipophilic balance).

In manufacturing the chewing gum including the active agent or ingredient, the active agent or medicament is added, preferably, early on in the mix. The smaller the amount of active ingredient used, the more necessary it becomes to preblend that particular ingredient to assume uniform distribution throughout the batch of gum. Whether a preblend is used or not, the active agent or medicament should be added within the first five minutes of mixing. For faster release, the active agent may be added late in the process.

Optionally, the chewing gum of the present invention may include additional breath freshening, anti microbial or oral health ingredients, such as food acceptable metallic salts selected from zinc and copper salts of gluconic acid, zinc and copper salts of lactic acid, zinc and copper salts of acetic acid, zinc and copper salts of citric acid and combinations thereof. Further, antimicrobial essential oils and flavor components such as peppermint, methyl salicylate, thymol, eucalyptol, cinnamic aldehyde, polyphosphate, pyrophosphate and combinations thereof may be added to the gum composition. Dental health ingredients, such as fluoride salts, phosphate salts, proteolytic enzymes, lipids, antimicrobial s, calcium, electrolytes, protein additives, dental abrasives and combinations thereof may also be added to the gum composition.

In general, the chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

Chewing gum base and chewing gum product have been manufactured conventionally using separate mixers, different mixing technologies and, often, at different factories. One reason for this is that the optimum conditions for manufacturing gum base, and for manufacturing chewing gum from gum base and other ingredients such as sweeteners and flavors, are so different that it has been impractical to integrate both tasks. Chewing gum base manufacture, on the one hand, involves the dispersive (often high shear) mixing of difficult-to-blend ingredients such as elastomer, filler, elastomer plasticizer, base softeners/emulsifiers and sometimes wax, and typically requires long mixing times. Chewing gum product manufacture, on the other hand, involves combining the gum base with more delicate ingredients such as product softeners, bulk sweeteners, high intensity sweeteners and flavoring agents using distributive (generally lower shear) mixing, for shorter periods.

During the chewing gum manufacturing process, the entire mixing procedure typically takes from five to fifteen minutes, but longer mixing times may sometimes be required. Those skilled in the art will recognize that many variations of the above described procedure may be followed.

Table 11 below lists examples of formulations of Magnolia Bark Extract in a chewing gum. Example 1 is a comparative example of a prior art gum formulation.

TABLE 11

Antimicrobial Gum Formulas (dry weight percent basis)

| Ingredient | Example 1 | Example 2 | Example 3 | Example 4 | Example 5 |
|---|---|---|---|---|---|
| Gum Base | 25.21 | 26.22 | 25.21 | 25.21 | 25.21 |
| Lecithin | 0.17 | 0.17 | 0.17 | 2.00 | 0.17 |
| NaHCO$_3$ | 0.25 | 0.25 | 0.25 | 0.25 | 0.25 |
| Sorbitol | 50.86 | 49.86 | 47.86 | 45.86 | 50.36 |
| MBE | — | 0.10 | 3.00 | 2.00 | 0.50 |
| Mannitol | 4.25 | 4.25 | 4.25 | 4.25 | 4.25 |
| Lycasin/Glycerin | 8.51 | 8.51 | 8.51 | 8.51 | 8.51 |
| Glycerin | 8.50 | 8.50 | 8.50 | 8.50 | 8.50 |
| Encapsulated Sweetener | 0.67 | 0.67 | 0.67 | 0.67 | 0.67 |
| Flavor | 1.58 | 1.58 | 1.58 | 1.58 | 1.58 |
| Total | 100.00 | 100.00 | 100.00 | 100.00 | 100.00 |

In accordance with the invention, each of the formulations in examples 2-5 is supplemented with a surface active agent as described above. In one exemplary formulation, each of the examples 2-5 includes about 0.01% to about 2% of a surface active agent as described above. In another exemplary formulation, each of the examples 2-5 includes about 25 ppm to about 500 ppm of a surface active agent as described above. In yet another exemplary formulation, each of the examples 2-5 includes about sodium lauryl sulfate and Magnolia Bark Extract in a ratio of about 1/4 to about 4/1.

Formulation Techniques

When formulating the relatively fast release compositions of this invention, any relevant controlled formulation technique for preparing an oral composition with controlled release may be applied. Thus, the dosage form may be in the form of a liquid having particles dispersed in a dispersion medium or it may be in the form of a single or a multiple unit dosage form intended for use as such as for dispersing in a dispersion medium before use.

For any use that requires fast release, the particle size reduction is essential to see the full benefit of the active. For many actives, there is a critical level required to obtain a response. Thus it is essential that at least an effective amount of the active be in small particle form. Effective amounts depend upon the active and the end result desired. For example, an active may be added to the gum coating, which is a water soluble matrix, such that during the chewing period, the active may be released quickly, resulting in a fast release. This would allow a chewing gum coating to be a carrier for an active, specifically for MBE and for a surface active agent. For instance, U.S. Pat. No. 6,645,535, incorporated by reference herein, discloses a coating made with a syrup having an antacid dispersed therein, resulting in a fast release of the antacid.

In the compositions described below, a person skilled in the art will know how to incorporate a part that gives rise to a relatively fast release of the active substance. As an example, such a part may be incorporated in an outermost coating layer comprising the active substance, or it may be incorporated in the form of pellets formulated without retarding agents neither in the cores nor in a coating.

Examples of different controlled release technologies are: single units based on coated matrix, double or triple compression, or multilayer coating; and multiple units including units having a controlled release coating, units having a controlled release matrix, units having a controlled release compression coating, and units with a multilayer coating.

In one aspect of the invention, coated matrix technology is used to coat a sparingly soluble and/or swellable polymer, in which Magnolia Bark Extract (MBE) and/or surface active agent is embedded, with an insoluble diffusion barrier. The diffusion of MBE is controlled by the matrix and the coat. It is possible to use an outer film layer containing MBE, which is applied on the coated matrix. Alternatively, enteric coated units can be embedded in the matrix.

In another aspect of the invention, a formulation based on double or triple compression contains a core of a polymer having Magnolia Bark Extract and surface active agent incorporated. This core is compression coated with a polymer with MBE incorporated in the same or another concentration than in the core. When triple compression is employed, the coated core is compression coated once more with a polymer with MBE in the same or another concentration as in the first coat. Finally, the double or triple compression unit is spray coated and MBE is incorporated in the coat. However, the concentrations of MBE in the different coats may vary markedly. When the MBE of the first layer has been almost depleted, the next layer takes over and levels out or changes the release profile.

In a multilayer coating formulation, an inert core is coated with several layers of diffusion barriers, each barrier containing different concentrations of MBE. The concentration should be highest in the inner coat and lowest in the outer coat. The purpose of the concentration gradient is to compensate for the increasing diffusion distance closer to the core. The thickness of the diffusion barriers and the concentration gradients need to be correctly adjusted. The multilayer technologies might be optimized by the use of an enteric polymer, and/or by the use of an amylose containing film coating such as a coating containing ethylcellulose and amylose. Furthermore, spray coating with Magnolia Bark Extract and surface active agent gives an immediate burst of the antimicrobial active(s).

Multiple unit systems may be used, comprising chewable pellets, granules, crystals, mini tablets or mixtures thereof. In such systems, some units may be uncoated, whereas other units may be formulated as a matrix or a coated matrix. The units can be compressed. The MBE and the surface active agent may also be present in the composition in the form of a multiplicity of individual units such as, for example chewable pellets, minitablets, and crystals of active substances. The two parts may be in admixture, or they may comprise at least two different types of chewable pellets, minitablets, or crystals, the first type of pellets corresponding to the first part and the second type of pellets corresponding to the second part. Alternatively, fast release according to the invention may also be obtained if individual units contain relatively large crystals of the active drug substance. In such cases, the unit size is typically in the micrometer range.

The fast release of MBE and surface active agent may be achieved with any compound which is a natural fast release compound, or it may be a compound which has been treated such that it will possess fast release properties during chewing. Treating methods contemplated include encapsulation, co-drying and dissolution of the MBE and the surface active agent into various solvents including water, alcohols, flavors, and the like.

In another embodiment of the invention, antimicrobial effect may be obtained when the actives are encapsulated within a biodegradable-biocompatible polymeric matrix, according to many of the microencapsulation teachings in the art. The microcapsules may be comprised of a core of polypeptide or other biologically active agent encapsulated in a matrix of poly(lactide/glycolide) copolymer.

The fast release of MBE and surface active agent may be accomplished with the use of detergent-compatible compositions. Types of compositions useful herein are detergent-compatible compositions containing softening particles such as those known in the art, including mixtures of organic dispersion inhibitors (for example, stearyl alcohol and fatty sorbitan esters).

In chewing gum manufacturing, fast release flavors may result when the flavors are encapsulated in gum arabic. In accordance with an aspect of the invention, fast release of Magnolia Bark Extract and surface active agent may be accomplished through their encapsulation in gum arabic.

In principle, controlled release of sweeteners in chewing gums is obtained by selecting sweeteners that are, by their nature, fast release sweeteners and those which are, by their nature, slow release sweeteners, and blending them with the gum base. Accordingly, the antimicrobial compositions of the invention can be blended with fast release sweeteners, to obtain the chewing gum of this invention having fast release of antimicrobial compounds during the chew.

Fast release sweeteners contemplated by the present invention include the low intensity sweeteners sucrose, dried invert sugar, fructose, xylitol, and combinations thereof. Fast release sweeteners also include most high intensity sweeteners including aspartame, acesulfame, alitame, saccharin, cyclamate, dihydrochalcones, alone or in any combination. Specifically excepted from this group are thaumatin and monellin which are considered to be slow release sweeteners. Further, those skilled in the art will recognize the low intensity sweeteners may also serve as bulking agents in the chewing gum in whole or in part. In addition, the softener may be combined with the low intensity sweeteners such as in an aqueous solution.

It should be noted that soft, chewable candies and tablets may be manufactured in layers. Accordingly, in another aspect of the invention, the antimicrobial compounds of the invention may be mixed into the ingredients of one or more of the layers, thereby providing for fast release of the active substance.

All of the above-mentioned combinations of different types of compositions or formulation techniques apply to the fast release part or composition of the invention. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A chewable product for freshening the breath of consumers of the chewable product, comprising a coating layer which includes a fast release antimicrobial agent comprising a synergistic ratio of a Magnolia bark extract and a surfactant, wherein the synergistic ratio is at least about 1 part Magnolia bark extract to 1 part surfactant.

2. The chewable product of claim 1 wherein the surfactant comprises a bactericidal surfactant.

3. The chewable product of claim 1 wherein the surfactant comprises a salt selected from the group consisting of a sodium salt and an ammonium salt.

4. The chewable product of claim 1 wherein the surfactant comprises an anionic surfactant.

5. The chewable product of claim 1 wherein the surfactant comprises about 0.001% to about 2% sodium lauryl sulfate by weight of the chewable product.

6. The chewable product of claim 1 wherein the synergistic ratio ranges from about 1 part Magnolia bark extract to 1 part surfactant up to about 4 parts Magnolia bark extract to 1 part surfactant.

7. The chewable product of claim 1 wherein the surfactant comprises sodium lauryl sulfate.

8. The chewable product of claim 7 wherein the synergistic ratio of Magnolia bark extract to sodium lauryl sulfate is about 2 parts Magnolia bark extract to 1 part sodium lauryl sulfate.

9. The chewable product of claim 1 wherein the surfactant comprises about 0.001% to about 1.0% of the chewable product.

10. The chewable product of claim 1 wherein the surfactant comprises a fatty acid or a glyceride 11. The chewable product of claim 1 comprising one of a chewing gum, or a chewable candy.

12. The chewable product of claim 1 wherein the fast release antimicrobial agent is encapsulated in gum arabic.

13. The chewable product of claim 1 wherein the fast release antimicrobial agent is encapsulated in a coated matrix, which is then included in the coating of the chewable product.

14. The chewable product of claim 1 wherein the fast release antimicrobial agent is included in a spray coating applied to the surface of the chewable product.

15. The chewable product of claim 1 wherein the fast release antimicrobial agent is included in a multilayer coating surrounding the chewable product.

16. The chewable product of claim 1 wherein the fast release antimicrobial agent is encapsulated by double compression or triple compression into the chewable product.

17. The chewable product of claim 1 wherein the chewable product is in the form of a multiple unit system.

18. The chewable product of claim 1 wherein the fast release antimicrobial agent is encapsulated in a biodegradable polymeric matrix, which is then included in the coating of the chewable product.

19. A chewable product comprising:
(a) a water insoluble portion;
(b) a water soluble portion; and
(c) a coating layer on the core of the chewable product, the coating layer including an effective amount of an antimicrobial agent comprising a synergistic ratio of a Magnolia bark extract and a surfactant, wherein the synergistic ratio is at least about 1 part Magnolia bark extract to 1 part surfactant.

20. A process for preparing a chewable product, the process comprising forming a coating by incorporating an antimicrobial agent comprising a synergistic ratio of at least about 1 part Magnolia bark extract to 1 part surfactant in the amount of about 0.05% to about 10% by weight of the chewable product, admixing the ingredients until a uniform mixture is obtained and thereafter applying the mixture as a coating on the chewable product.

21. The chewable product of claim 1 wherein the oral composition is a chewing gum.

22. The chewable product of claim 19 wherein the oral composition is a chewy candy.

23. The process of claim 20 wherein the chewable product is a chewing gum.

24. The chewable product of claim 1 wherein the coating layer on the core of the chewable product includes a fast release antimicrobial agent comprising a synergistic ratio of a Magnolia bark extract and a surfactant, wherein the synergistic ratio ranges from about 1 part Magnolia bark extract to 1 part surfactant up to about 4 parts Magnolia bark extract to 1 part surfactant.

25. The chewable product of claim 19 wherein the coating layer on the core of the chewable product includes a fast release antimicrobial agent comprising a synergistic ratio of a Magnolia bark extract and a surfactant, wherein the synergistic ratio ranges from about 1 part Magnolia bark extract to 1 part surfactant up to about 4 parts Magnolia bark extract to 1 part surfactant.

* * * * *